United States Patent [19]
Zachariades

[11] Patent Number: 4,587,163
[45] Date of Patent: May 6, 1986

[54] PREPARATION OF ULTRA HIGH MOLECULAR WEIGHT POLYETHYLENE MORPHOLOGIES OF TOTALLY FUSED PARTICLES WITH SUPERIOR MECHANICAL PERFORMANCE

[76] Inventor: Anagnostis E. Zachariades, 65 Glen Garry Way, Hillsborough, Calif. 94010

[21] Appl. No.: 667,020

[22] Filed: Nov. 1, 1984

Related U.S. Application Data

[63] Continuation-in-part of Ser. No. 586,796, Mar. 6, 1984, abandoned.

[51] Int. Cl.$^4$ .............................................. B32B 27/32
[52] U.S. Cl. ................................... 428/292; 128/92 C; 264/280; 264/331.17; 264/348; 428/364; 526/352; 528/481; 528/950
[58] Field of Search ...................... 3/1, 1.9; 128/92 C; 264/85, 175, 280, 320, 322, 331.17, 348; 428/292, 364, 523, 910; 526/352; 528/481, 950

[56] References Cited

U.S. PATENT DOCUMENTS

| | | | |
|---|---|---|---|
| 4,055,862 | 11/1977 | Farling | 264/126 |
| 4,116,892 | 9/1978 | Schwarz | 428/910 |
| 4,164,531 | 8/1979 | Shiraki et al. | 264/328.7 |
| 4,489,033 | 12/1984 | Uda et al. | 264/328.7 |

Primary Examiner—William J. Van Balen
Attorney, Agent, or Firm—Owen, Wickersham & Erickson

[57] ABSTRACT

An isotropic semicrystalline morphology of ultra-high-molecular-weight polyethylene and a method of making it. An original powder stock or a partially fused, melt-crystallized stock having a granular memory, is heated to a temperature at which the stock fuses completely to form a homogeneous melt which loses memory of the granular structure of the original stock. The resultant melt is cooled to ambient temperatures under compression to provide a novel homogeneous isotropic semicrystalline morphology. An anisotropic morphology of ultra-high-molecular-weight polyethylene may then be made by solid-state deforming that semicrystalline morphology at a temperature near but below its crystalline melting point at a deformation ratio of about 5 to 8.

19 Claims, 4 Drawing Figures

FIG. 3

5x DRAWN MORPHOLOGIES FROM COMPRESSION MOLDED SPECIMEN AT
(a) 320°C
(b) 180°C

FIG. 4

PREPARATION OF ULTRA HIGH MOLECULAR WEIGHT POLYETHYLENE MORPHOLOGIES OF TOTALLY FUSED PARTICLES WITH SUPERIOR MECHANICAL PERFORMANCE

CROSS REFERENCES TO RELATED APPLICATIONS

This application is a continuation-in-part of application Ser. No. 586,796, filed Mar. 6,1984 abandoned.

Co-pending patent application Ser. No. 578,171, filed Feb. 8, 1984, abandoned, relates to a solid state deformation process for achieving the production of high modulus and high-strength polymers in simple and complex shapes at rapid output rates and moderate processing conditions.

FIELD OF THE INVENTION

This invention relates to a novel type of ultra-high-molecular-weight polyethylene with superior modulus and elastic response performance and the method of making it.

Ultra-high molecular weight polyethylene has been defined by ASTM as those linear polyethylenes which have a relative viscosity of 2.3 or greater at a solution concentration of 0.05% at 125° C. in decahydronaphthlaene. The nominal weight-average molecular weight is several million, usually from three to six million.

BACKGROUND OF THE INVENTION

Various polymer systems have been investigated for such uses as the preparation of artificial prostheses for biomedical, particularly orthopedic applications. The objective has usually been to duplicate the mechanical properties of the natural counterparts and to meet the requirements of tissue biocompatibility. For example, the preparation of artificial tendons has been pursued basically by the construction of composite structures of fiber-reinforced elastomers, such as poly(ethylene terephthalate) in silicone rubber. Silk and metal fibers have also been used as components in such prostheses. The fabrication of tapes and fiber meshes using conventional polymers, e.g., nylon, dacron, and polyethylene has also been explored. In the latter case, however, nylon has been found to degrade in vivo; dacrons have been found to fail in tissue ingrowth tests; and conventional polyethylene when strained in the working range of human tendons (3% strain), has been unsatisfactory both in its elastic recovery (80–90%) and in the time needed for complete recovery (5 min.)—two important factors in the design of artificial tendons.

Ligament fabrication has been pursued by the design of artificial preparations utilizing ultra-high-molecular-weight polyethylene. Ultra-high molecular weight polyethylene, in contrast to the conventional high-density polyethylenes having average molecular weight up to about 400,000, has an extremely high molecular weight—typically 2 to 6 million—and is intractable. The polymer is supplied as fine powder and is processed into various profiles using compression molding and ram extrusion processes. However, studies made heretofore have suggested that the ultra-high molecular weight polyethylene structures made by such processes do not possess adequate yield, creep, and fatigue properties to meet the requirements of biomedical applications, apparently because of poor interparticle fusion of the powder particles in the raw material during its processing. More recently, new processing systems, including ultra-high speed mixing systems and radio-frequency heating, have been used in injection molding practices to produce ultra-high molecular weight products. However, the products of such processes are obtained also in a temperature range (360°–380° F. 182°–193° C.) in which it has been found that complete fusion of the powder particles does not occur. Furthermore, radio-frequency heating, an effective process for heating polymers such as nylons, PVC, and $PVF_2$ that have polar molecules to respond to radio-frequency energy is impractical for non-polar polymers such as polyethylene. Radio-frequency heating of such polymers can occur by incorporating in the polymer agents such as Frequon (a trademark of the Phillips Chemical Co.) which are sensitive to radio frequency. However, the use of additives in the polymer, which is known to be biocompatible, may have adverse effects in meeting the requirements of tissue biocompatibility in biomedical applications.

SUMMARY OF THE INVENTION

This invention provides the complete fusion of powder particles of ultra-high molecular weight polyethylene in an hitherto unexplored temperature range, resulting in a homogeneously melt crystallized morphology with no grain memory of the powder particles and the preparation of an anisotropic morphology with significantly enhanced modulus and superior elastic response performance by solid state deformation techniques.

The present invention provides a homogeneously melt-crystallized morphology of ultra-high molecular polyethylene obtained by complete fusion of the powder particles of the raw material in a temperature range in which the powder particles fuse completely and have no memory of their granular structure prior to melting and during the inadequate melting which is practiced in currently used processes. The mechanical performance of such homogeneous melt crystallized morphologies of ultra-high molecular weight polyethylene are superior to the properties of commercially available products of ultra-high molecular weight polyethylene.

This invention provides also the preparation of an anisotropic morphology of ultra-high molecular weight polyethylene with significantly enhanced modulus and superior elastic response performance by the solid state deformation techniques of drawing and extrusion through an extrusion rolling die. This performance has been demonstrated both in laboratory testing and in vivo functional loads for biomedical applications.

According to the present invention, the preparation of the anisotropic morphology of ultra-high-molecular-weight polyethylene comprises the steps of (1) preparing initially a uniform semicrystalline morphology by compression-molding an ultra-high molecular-weight polyethylene melt in a temperature range in which the melt has no memory of the granular nature of the original powder, and (2) solid-state deforming the so-produced uniformly melt-crystallized morphology by conventional drawing or by extruding it through an extrusion rolling die at a temperature preferably near but below its crystalline melting point and at a deformation ratio of 5–8. The deformation ratio is determined by the displacement of printed markers or fiducial marks on the surface of the drawn or extruded specimen or the cross-sectional areas of the samples before and after drawing or extrusion.

DESCRIPTION OF SOME PREFERRED EMBODIMENTS OF THE INVENTION

An ultra-high-molecular-weight polyethylene melt, in which the powder particles fuse completely and lose memory of their granular structure in the original powder stock, is achieved by heating the powder stock or partially fused, melt-crystallized morphology having granular memory—in the absence of oxygen to avoid degradation, e.g., under nitrogen—in a temperature range above 220° C. and below 340° C. the latter being the temperature at which excessive decomposition occurs under nitrogen. Isobaric heating at 320° C. under a compression load of 1500–2000 lbs. for 10 minutes followed by heating at 150° C. under a load of 12000–14000 lbs. for an additional 10 minutes and cooling to ambient under the same compression conditions results in a uniform or homogeneous melt-crystallized morphology with no grain memory. The resultant ultra-high molecular weight polyethylene morphology has superior mechanical performance in comparison to currently available products which are fabricated typically in the temperature range of 180–210° C. and under similar pressure conditions.

Prior literature dictates that under these temperature and pressure conditions the powder particles should fuse completely. (The equilibrium melting temperature of ideal crystals of polyethylene is 141.4° C.). However, in the case of ultra-high molecular weight polyethylene such processing conditions result in a partial fusion as manifested from the grain memory of the original powder particles and the diminished mechanical properties. Complete fusion of the powder particles of ultra-high molecular weight polyethylene and consequently a uniform melt-crystallized morphology occurs by heating above 220° C. and results in superior mechanical properties in comparison to the properties exhibited by the prepared morphologies below 220° C., i.e., 180°–210° C. Alternatively, a partially fused, melt-crystallized morphology with granular memory, typically obtained at temperatures below 220° C., can be heated above 220° C. to obtain the complete fusion of this invention.

The partial fusion of the powder particles below 220° C. arises from the high melt viscosity (in the temperature range 145°–210° C.) which hinders the formation of a molecular network between powder particles and to the high degree of physical entanglements which hinder chain mobility during the compression molding process; effective chain interpenetration between powder particles can occur upon heating the raw powder stock or a partially fused melt-crystallized stock with granular memory above 220° C. where the melt viscosity is significantly lower.

Figure 1:
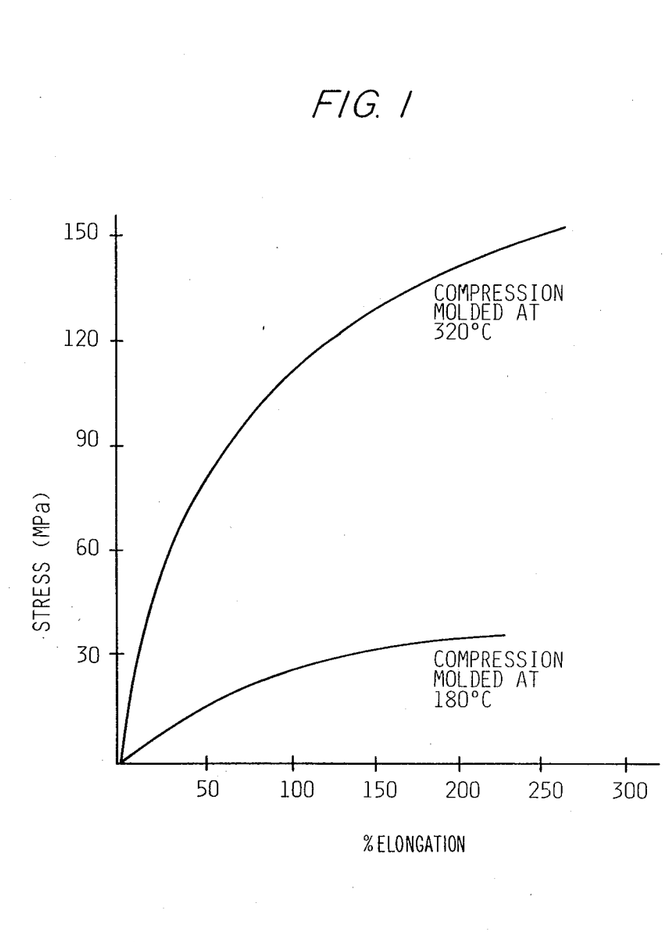
FIG. 1 is a graph showing the stress-elongation behavior at ambient temperature of two compression-molded specimens of ultra-high molecular weight polyethylene, one molded at 180° C. and the other according to the present invention, at 320° C.

As shown in FIG. 1, the presence of a molecular network between powder particles in the compression molded specimen at 320° C. results in a significantly higher slope of stress to extension and strength to break (150 MPa), in comparison to a specimen molded at 180° C. which is comprised of partially fused powder particles and which fractured at 35–40 MPa.

Solid-state deformation of such homogeneously melt-crystallized morphologies previously prepared by compression molding at 320° C. take place by drawing or extrusion through an extrusion rolling die at 130° C. and a deformation ratio 5–8 and result in anisotropic morphologies with superior mechanical properties in comparison to the five-times-drawn morphologies obtained by solid-state deformation of compression-molded at 180°–200° C. For example, as shown in FIG. 2, the slope of stress to elongation of an anisotropic morphology of a five-times-drawn ultrahigh molecular weight polyethylene sample prepared by compression molding at 320° C., is considerably higher than the slope of a five-times-drawn sample from a compression molded specimen at 210° C., and significantly higher than the slope of a five-times-drawn sample from a compression molded specimen at 180° C., evidently reflecting the higher degree of interparticle chain penetration which occurs by compression molding at higher temperatures.

Figure 2:
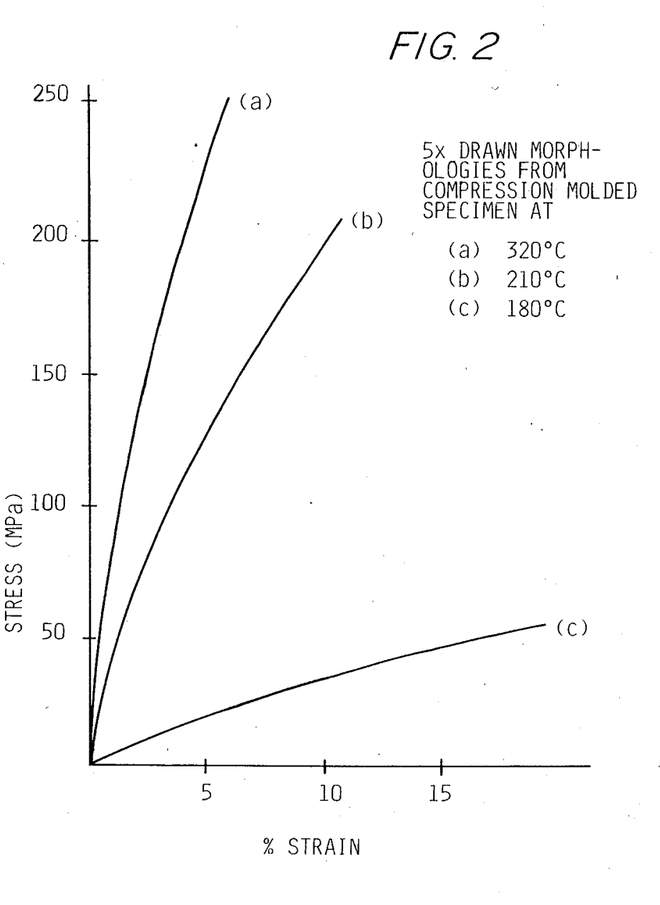
FIG. 2 is a similar graph contrasting the stress-strain behavior of three specimens of five-times-drawn ultra-high molecular weight polyethylene obtained by solid-state deforming of compression molded specimens at 180° C., and 210° C., and, according to the present invention, at 320° C.
Figure 3:
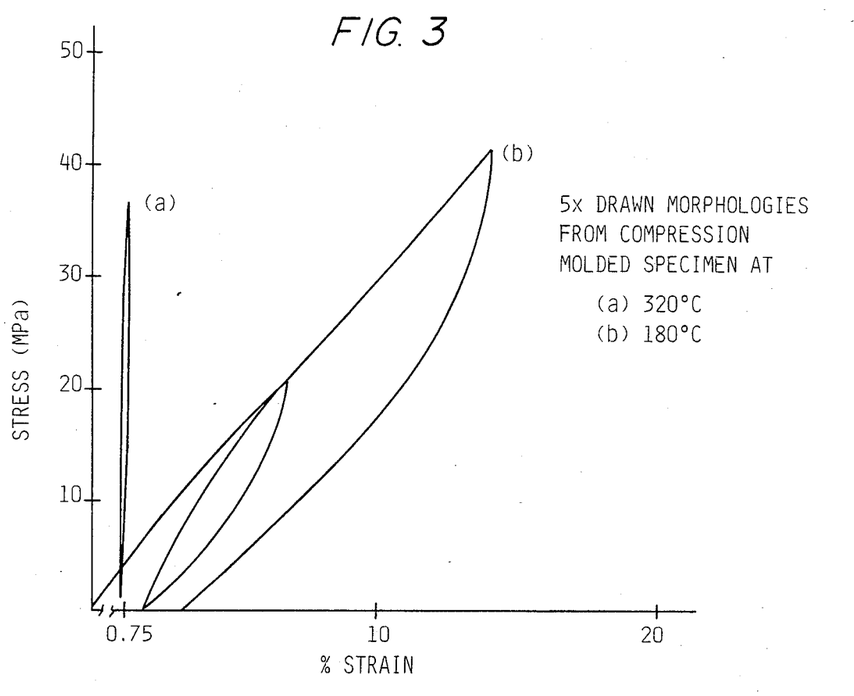
FIG. 3 is a similar drawing, showing the stress-strain behavior under cyclic load tests at ambient temperatures of five-times-drawn ultra-high molecular weight polyethylene morphologies obtained by solid-state deformation of a compression-molded specimen at 180° C. and, according to the present invention, at 320° C.

The overall increase in the slope of load-to-elongation observed in FIG. 2, in comparison to the undrawn morphologies in FIG. 1, is associated with the chain extension and orientation of the five-times-drawn morphologies. The five-times-drawn morphologies from specimens compression molded at 320° C. have a Young modulus of 5–6 GPa, and in cyclic load tests under 40–45 MPa for testing up to 1 hour they deform practically elastically (see FIG. 3). On the contrary, as also shown in FIG. 3, the five-times-drawn morphologies from specimens compression molded at 180° C. have a low Young modulus (0.7–0.8 GPa) and in cyclic load tests under the same conditions undergo a maximum residual elongation greater than 3%.

Tests In vivo indicate that artificial tendons made by this process can be sutured to the natural tendon segments readily and without fibrillation. It is significant that the ultra-high-molecular-weight polyethylene anisotropic morphologies in this invention do not exhibit a tendency to fibrillation, for this is in contrast to the fibrillation observed with conventional-molecular-weight (60,000 to 400,000) polyethylene analogues. Anisotropic products are strong only in the drawn direction in which the molecular chains are oriented and connected by covalent bonds but are extremely weak in their lateral direction because the chains are connected by weak Van der Waals forces, and consequently when a load is applied perpendicularly to the direction of chain orientation they tend to fibrillate along the chain direction. Although cross-linking by radiation or chemical additives have been used to alleviate the occurence of fibrillation, the resistance to fibrillation of the ultra-high molecular weight polyethylene anisotropic morphology in this invention is due to the excessive amount of physical entanglement in the so-prepared initially homogeneous melt crystallized morphology.

Figure 4:
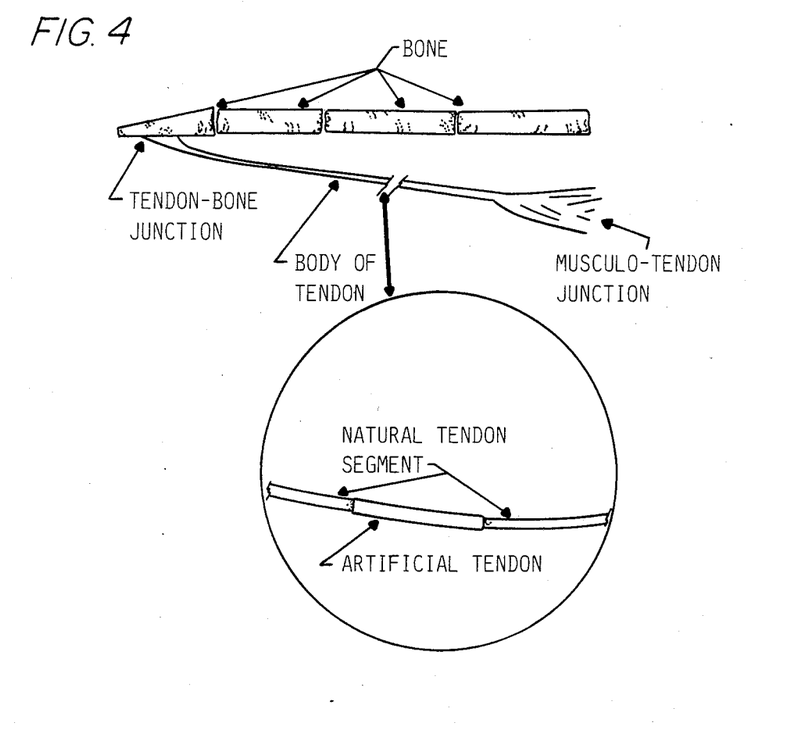
FIG. 4 is a diagrammatic cross-sectional view of a flexor tendon and related parts, employing the principles of this invention, indicating the tendon-bone and the muscle-tendon functions and the body of the tendon which was truncated to insert and suture the artificial tendon of ultra-high molecular weight polyethylene of this invention.

Artificial tendons made according to the present invention exhibit very satisfactory anastomosis after an observation period of six weeks, and they replicate the properties of the natural tendons. For example, they have been found to replicate the properties of the tendon (Flexor Hollucis longus) of a dog weighing approximately 70 pounds, as demonstrated by the complete mobility of the dog during the six-week testing period. A lateral view of a flexor tendon indicating the tendon-bone and the musculo-tendon junctions and the body of the tendon which was truncated to insert and suture the artificial tendon of ultra-high molecular weight polyethylene is shown in FIG. 4.

The present invention also includes within its scope the use of the isotropic (the initially homogeneous melt-crystallized morphology, prepared from either a raw powder stock or a partially fused melt-crystallized stock with granular memory, prior to drawing or extrusion) and anisotropic ultra-high-molecular-weight polyethylene morphologies in other biomedical applications, e.g., ligament prostheses in which a high elastic recovery and a small percent strain under high load requirements are necessary. Furthermore, the homogeneity of the morphologies in this invention versus the partially fused morphologies used to date, is important in eliminating the fatigue failure observed with orthopedic prostheses which are fabricated from partially fused morphologies and also in the fabrication of orthopedic prostheses with abrasion resistance uses such as joints and intervertebral disks.

Other applications on which the homogeneity of the morphologies in this invention is important, is in the fabrication of industrial parts with abrasion resistance uses such as bearings, sprockets, gaskets, ball valve seats, conveyor belt parts and other industrial parts currently made from metal.

To those skilled in the art to which this invention relates, many changes in construction and widely differing embodiments and applications of the invention will suggest themselves without departing from the spirit and scope of the invention. The disclosures and the descriptions herein are purely illustrative and are not intended to be in any sense limiting.

What is claimed is:

1. A method for making an isotropic semicrystalline morphology of ultra-high-molecular-weight polyethylene comprising:
   heating an original powder stock or a partially fused melt-crystallized stock having granular memory to a temperature and for a time to fuse the stock completely to form a homogeneous melt which has lost memory of its former granular structure, and
   cooling the resultant melt to ambient temperatures under compression to provide a homogeneous isotropic semicrystalline morphology which has no memory of the granular nature of the original stock.

2. The method of claim 1 wherein the heating step comprises heating to 220°-320° C. for about 10 minutes.

3. A method for making an isotropic homogeneous semicrystalline morphology of ultra-high-molecular-weight polyethylene comprising;
   heating an original powder stock or a partially fused melt-crystallized stock having granular memory, to a temperature between 220° C. and 320° C. in the absence of oxygen at a compression load of about 1500–2000 pounds for about ten minutes,
   then at about 150° C. placing the material under a compression load of about 12000–14000 pounds for another ten minutes to provide a melt in which the stock fuses completely and loses memory of its former granular structure, and
   cooling the resultant material to ambient temperatures under a compression load of about 1500 pounds to give a semicrystalline morphology which has no memory of the granular nature of the original stock.

4. A method for making an anisotropic morphology of ultra-high-molecular-weight polyethylene comprising:
   heating an original powder stock or a partially fused melt-crystallized stock having granular memory to a temperature and for a time to fuse the stock completely and lose memory of its original granular structure,
   cooling the resultant material to ambient temperatures under compression to provide an initial homqgenous isotropic semicrystalline morphology which has no memory of the granular nature of the original stock, and
   solid-state deforming that semicrystalline morphology at a temperature near but below its crystalline melting point at a deformation ratio of about 5 to 8.

5. The method of claim 4 wherein the temperature of deformation is about 130° C.

6. The method of claim 4 wherein the heating step includes heating at 220° C. to 320° C. for about ten minutes under a compression load of about 1500–2000 pounds.

7. The method of claim 6 wherein the heating step also includes subsequently, at about 150° C. applying a load of about 12000–14000 pounds for about ten minutes.

8. The method of claim 4 wherein the deforming step includes at least five times.

9. A method for making an anisotropic morphology of ultra-high-molecular-weight polyethylene comprising:
   heating an original powder stock or a partially fused, melt-crystallized stock having granular memory, to a temperature between 220° C. and 320° C. in the absence of oxygen at a compression load of about 1500–2000 pounds for about ten minutes,
   then at about 150° C. placing the material under a compression load of about 12000–14000 pounds for another ten minutes to provide a melt in which the stock fuses completely and loses memory of its former granular structure,
   cooling the resultant material to ambient temperatures under a compression load of about 1500 pounds to give a semicrystalline morphology which has no memory of the granular nature of the original stock, and
   extruding the semicrystalline product through an extrusion rolling die at a temperature of about 130° C. at a deformation ratio of about 5 to 8.

10. A method for making an anisotropic morphology of ultra-high-molecular-weight polyethylene comprising:

heating an original powder stock or a partially fused, melt-crystallized stock having a granular memory, to a temperature between 220° C. and 320° C. in the absence of oxygen at a compression load of about 1500–2000 pounds for about ten minutes, then at about 150° C. placing the material under a compression load of about 12000–14000 pounds for another ten minutes to provide a melt in which the stock fuses completely and loses memory of its former granular structure, cooling the resultant material to ambient temperatures under a compression load of about 1500 pounds to give a semicrystalline morphology which has no memory of the granular nature of the original stock, and drawing the semicrystalline product at a temperature of about 130° C. at a deformation ratio of about 5 to 8.

11. An isotropic semicrystalline morphology of ultra-high-molecular-weight polyethylene comprising a completely fused ultra-high molecular weight polyethylene without any memory of a granular structure.

12. An isotropic semicrystalline morphology of ultra-high-molecular-weight polyethylene obtained from a homogeneous melt of ultra-high molecular weight polyethylene with weight average molecular weight of several millions without the aid of radiation dopants.

13. A homogeneous melt crystallized ultra-high molecular-weight polyethylene morphology with an effective molecular network structure and number of physical entanglements without the aid of radiation cross linking or chemical cross linking agents.

14. An ultra-high-molecular-weight polyethylene useful for tendon fabrication, having a molecular weight of several million and made by first heating an original powder stock or a partially fused, melt-crystallized stock having a granular memory, to a temperature at which the stock fuses completely and loses memory of its former granular structure, and then cooling the resultant material to ambient temperatures under compression load to give a semicrystalline morphology without memory of the granular nature of the original stock.

15. An anisotropic morphology of ultra-high-molecular-weight polyethylene comprising:

a solid-state deformed semicrystalline morphology, having no memory of a granular nature, deformed at a temperature near but below its crystalline melting point at a deformation ratio of about 5 to 8.

16. The anisotropic morphology of ultra-high-molecular-weight polyethylene in claim 15 wherein the solid state deformed morphology is filamentary or ribbon-like.

17. The anisotropic morphology of ultra-high-molecular-weight polyethylene in claim 16 wherein the filamentary or ribbon-like products exhibit resistance to fibrillation without the aid of radiation cross-linking or chemical cross-linking agents.

18. An ultra-high-molecular-weight polyethylene useful for tendon fabrication, having a molecular weight of several million and made by first heating an original powder stock or a partially fused, melt-crystallized stock having a granular memory, to a temperature at which the stock fuses completely and loses memory of its former granular structure, then cooling the resultant material to ambient temperatures under compression load to give a semicrystalline morphology without memory of the granular nature of the original stock, and then extruding the semicrystalline product through an extrusion rolling die at a temperature of about 130° C. and at a deformation ratio of about 5–8.

19. An ultra-high-molecular-weight polyethylene useful for tendon fabrication, having a molecular weight of several million and made by first heating an original powder stock or a partially fused, melt-crystallized stock having a granular memory, to a temperature at which the stock fuses completely and loses memory of its former granular structure, then cooling the resultant material to ambient temperatures under compression load to give a semicrystalline morphology without memory of the granular nature of the original stock, and then drawing the semicrystalline product at a temperature of about 130° C. and at a deformation ratio of about 5–8.

* * * * *

UNITED STATES PATENT AND TRADEMARK OFFICE
CERTIFICATE OF CORRECTION

PATENT NO. : 4,587,163
DATED : May 6, 1986
INVENTOR(S) : Anagnostis E. Zachariades It is certified that error appears in the above-identified patent and that said Letters Patent are hereby corrected as shown below:

Column 1, lines 26-27, "decahydronaphthlaene" should read

--decahydronaphthalene--.

Column 5, line 2, "occurence" should read --occurrence--.

Column 6, line 30, which is line 11 of claim 4, "homqgenous"

should read --homogeneous--.

Column 6, 19ne 47, which is line 2 of claim 8, "includes"

should read --includes drawing--.

Signed and Sealed this

Sixteenth Day of September 1986

[SEAL]

Attest:

DONALD J. QUIGG

Attesting Officer   Commissioner of Patents and Trademarks

REEXAMINATION CERTIFICATE (1238th)

United States Patent [19]

Zachariades

[11] B1 4,587,163

[45] Certificate Issued Apr. 3, 1990

[54] PREPARATION OF ULTRA HIGH MOLECULAR WEIGHT POLYETHYLENE MORPHOLOGIES OF TOTALLY FUSED PARTICLES WITH SUPERIOR MECHANICAL PERFORMANCE

[76] Inventor: Anagnostis E. Zachariades, 65 Glen Garry Way, Hillsborough, Calif. 94010

Reexamination Request:
No. 90/001,568, Aug. 1, 1988

Reexamination Certificate for:
Patent No.: 4,587,163
Issued: May 6, 1986
Appl. No.: 667,020
Filed: Nov. 1, 1984

[51] Int. Cl.⁴ ............................................. B32B 27/32
[52] U.S. Cl. ................................. 428/292; 128/92 C; 264/280; 264/331.17; 264/348; 428/364; 526/352; 528/481; 528/950
[58] Field of Search ......... 128/92 C; 264/280, 331.17, 264/348; 428/364; 526/352; 528/481, 950

[56] References Cited

U.S. PATENT DOCUMENTS 3,883,631  5/1975  Murray .............................. 264/210.2

OTHER PUBLICATIONS

Polymer Journal, vol. 14, No. 10, pp. 757–766, 1982, "Hot Drawing of Ultrahigh Molecular Weight Polyethylene", Kaito.

Textbook of Polymer Science (Second Edition), Billmeyer, 1962, N.Y., "Plastics Technology", pp. 491–493.

The Effect of Particle Characteristics on the Sintering Behavior of Ultra-High Molecular Weight Polyethylene, Halldin & Mehta, pp. 238–241 (no date).

Polymer Engineering & Science, vol. 20, No. 8, May 1980, pp. 555–561, "Solid State Extrusion of Ultra High Molecular Weight Polyethylene, Processing and Properties", Zachariades, Watts & Porter.

Journal Polymer Science: Polymer Physics Edition, vol. 21, 821–830 (Jun. 1983), "The Melt Anisotropy of Ultrahigh-Molecular-Weight Polyethylene", Zachariades & Logan.

Modern Plastics Encyclopedia, 1974–1975, Special International Supplement, pp. 558–559.

Modern Plastics Encyclopedia, Oct. 1979, vol. 56, No. 10A, pp. 514–515.

Primary Examiner—William J. Van Balen

[57] ABSTRACT

An isotropic semicrystalline morphology of ultra-high-molecular-weight polyethylene and a method of making it. An original powder stock or a partially fused, melt-crystallized stock having a granular memory, is heated to a temperature at which the stock fuses completely to form a homogeneous melt which loses memory of the granular structure of the original stock. The resultant melt is cooled to ambient temperatures under compression to provide a novel homogeneous isotropic semicrystalline morphology. An anisotropic morphology of ultra-high-molecular-weight polyethylene may then be made by solid-state deforming that semicrystalline morphology at a temperature near but below its crystalline melting point at a deformation ratio of about 5 to 8.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 1, lines 24–29.

Ultra-high molecular weight polyethylene has been defined by ASTM as those linear polyethylenes which have a relative viscosity of 2.3 or greater at a solution concentration of 0.05% at [125° C.] *135°* C. in [decahydronaphthl-aene] *decahydronaphthalene*. The nominal weight-average molecular weight is several million, usually from three to six million.

AS A RESULT OF REEXAMINATION, IT HAS BEEN DETERMINED THAT:

Claims 1–4, 6, 9–15, 18 and 19 are determined to be patentable as amended.

Claims 5, 7, 8, 16 and 17, dependent on an amended claim, are determined to be patentable.

New claims 20–22 are added and determined to be patentable.

1. A method for making an isotropic semicrystalline morphology of ultra-high-molecular-weight polyethylene comprising:

heating an original powder stock or a partially fused melt-crystallized stock, *each stock having a relative viscosity of 2.3 or greater at a solution concentration of 0.05% at 135°* C. in decahydronaphthalene having granular memory to a temperature *range of 220°–320°* C. *in the absence of oxygen* and for a time to fuse the stock completely to form a homogeneous melt which has lost memory of its former granular structure, and cooling the resultant melt to ambient temperatures under compression to provide a homogeneous isotropic semicrystalline morphology which has no memory of the granular nature of the original stock.

2. The method of claim 1 wherein the heating step comprises heating [to 220°–] *at* 320° C. for about 10 minutes.

3. A method for making an isotropic homogeneous semicrystalline morphology of ultra-high-molecular-weight polyethylene comprising;

heating an original powder stock or a partially fused melt-crystallized stock, *each stock having a relative viscosity of 2.3 or greater at a solution concentration of 0.05% at 135° C. in decahydronaphthalene,* having granular memory, [to] *at* a temperature [between 220° C. and ] *of about* 320° C. in the absence of oxygen at a compression load of about 1500–2000 pounds for about ten minutes, then at about 150° C. placing the material under a compression load of about 12000–14000 pounds for another ten minutes to provide a melt in which the stock fuses completely and loses memory of its former granular structure, and cooling the resultant material to ambient temperatures under a compression load of about 1500 pounds to give a semicrystalline morphology which has no memory of the granular nature of the original stock.

4. A method for making an anisotropic morphology of ultra-high-molecular-weight polyethylene comprising:

heating an original powder stock or a partially fused melt-crystallized stock, *each stock having a relative viscosity of 2.3 or greater at a solution concentration of 0.05% at 135° C. in decahydronaphthalene,* having granular memory, to a temperature *range of 220°–320°* C. *in the absence of oxygen* and for a time to fuse the stock completely and lose memory of its original granular structure, cooling the resultant material to ambient temperatures under compression to provide an initial homogenous isotropic semicrystalline morphology which has no memory of the granular nature of the original stock, and solid-state deforming that semicrystalline morphology at a temperature near but below its crystalline melting point at a deformation ratio of about 5 to 8.

6. The method of claim 4 wherein the heating step includes heating at [220° C. to] 320° C. for about ten minutes under a compression load of about 1500–2000 pounds.

9. A method for making an anisotropic morphology of ultra-high-molecular-weight polyethlene comprising:

heating an original powder stock or a partially fused, melt-crystallized stock, *each stock having a relatively viscosity of 2.3 or greater at a solution concentration of 0.05% at 135° C. in decahydronaphthalene,* having granular memory, to a temperature [between 220° C. and] *of about* 320° C. in the absence of oxygen at a compression load of about 1500–2000 pounds for about ten minutes, then at about 150° C. placing the material under a compression load of about 12000–14000 pounds for another ten minutes to provide a melt in which the stock fuses completely and loses memory of its former granular structure, cooling the resultant material to ambient temperatures under a compression load of about 1500 pounds to give a semicrystalline morphology which has no memory of the granular nature of the original stock, and extruding the semicrystalline product through an extrusion rolling die at a temperature of about 130° C. at a deformation ratio of about 5 to 8.

10. A method for making an anisotropic morphology of ultra-high-molecular-weight polyethylene comprising:

heating an original powder stock or a partially fused, melt-crystallized stock, *each stock having a relative viscosity of 2.3 or greater at a solution concentration of 0.05% at 135° C. in decahydronaphthalene,* having a granular memory, to a temperature [between 220° C. and] *of about* 320° C. in the absence of oxygen at a compression load of about 1500–2000 pounds for about ten minutes, then about 105° C. placing the material under a compression load of about 12000–14000 pounds for another ten minutes to provide a melt in which the stock fuses completely and loses memory of its former granular structure, cooling the resultant material to ambient temperatures under a compression load of about 1500 pounds to give a semicrystalline morphology which has no memory of the granular nature of the original stock, and drawing the semicrystalline product at a temperature of about 130° C. at a deformation ratio of about 5 to 8.

11. An isotropic semicrystalline morphology of ultra-high-molecular-weight polyethylene *from an original powder stock or a partially fused, melt-crystallized stock, each stock having a relative viscosity of 2.3 or greater at a solution concentration of 0.05% at 135°* C. in decahydronaphthalene comprising a completely fused ultra-high molecular weight polyethylene without any memory of a granular structure.

12. An isotropic semicrystalline morphology of ultra-high-molecular-weight polyethylene *from an original powder stock or a partially fused, melt-crystallized stock, each stock having a relative viscosity of 2.3 or greater at a solution concentration of 0.05% at 135°* C. in decahydronaphthalene obtained from a homogeneous melt of ultra-high molecular weight polyethylene with weight average molecular weight of several millions without the aid of radiation dopants.

13. A homogeneous melt crystallized ultra-high molecular-weight polyethylene morphology *from an original powder stock or a partialy fused, melt-crystallized stock, each stock having a relative viscosity of 2.3 or greater at a solution concentration of 0.05% at 135° C. in decahydronaphthalene* with an effective molecular network structure and number of physical entanglements without the aid of radiation cross linking or chemical cross linking agents.

14. An ultra-high-molecular-weight polyethylene useful for tendon fabrication, having a molecular weight of several million and made by first heating an original powder stock or a partially fused, melt-crystallized stock *each stock having a relative viscosity of 2.3 or greater at a solution concentration of 0.05% at 135° C. in decahydronaphthalene,* having a granular memory, to a temperature at which the stock fuses completely and loses memory of its former graunlar structure, and then cooling the resultant material to ambient temperatures under compression load to give a semicrystalline morphology without memory of the granular nature of the original stock.

15. An anisotropic morphology of ultra-high-molecular-weight polyethylene *from an original powder stock or a partially fused, melt-crystallized stock, each stock having a relative viscosity of 2.3 or greater at a solution concentration of 0.05% at 135° C. in decahydronaphthalene,* comprising:

a solid-state deformed semicrystalline morphology, having no memory of a granular nature, deformed at a temperature near but below its crystalline melting point at a deformation ratio of about 5 to 8.

18. An ultra-high molecular-weight polyethylene useful for tendon fabrication, having a molecular weight of several million and made by first heating *in the absence of oxygen* an original powder stock or a partially fused, melt-crystallized stock *each stock having a relative viscosity of 2.3 or greater at a solution concentration of 0.05% at 135° C. in decahydronaphthalene,* having a granular memory, to a temperature at which the stock fuses completely and loses memory of its former granular structure, then cooling the resultant material to ambient temperatures under compression load to give a semicrystalline morpholgy without memory of the granular nature of the original stock, and then extruding the semicrystalline product through an extrusion rolling die at a temperature of about 130° C. and at a deformation ratio of about 5–8.

19. An ultra-high-molecular-weight polyethylene useful for tendon fabrication, having a molecular weight of several million and made by first heating *in the absence of oxygen* an original powder stock or a partially fused, melt-crystallized stock, *each stock having a relative viscosity of 2.3 or greater at a solution concentration of 0.05% at 135° C. in decahydronaphthalene,* having a granular memory, to a temperature at which the stock fuses completely and loses memory of its former granular structure, then cooling the resultant material to ambient temperatures under compression load to give a semicrystalline morphology without memory of the granular nature of the original stock, and then drawing the semicrystalline product at a temperature of about 130° C. and at a deformation ratio of about 5–8.

20. *A method for making an isotropic homogeneous semicrystalline morphology of ultra-high molecular-weight polyethylene comprising:* heating an original powder stock or a partially fused melt-crystallized stock having a granular memory to a temperature between 220° C. and 320° C. in the absence of oxygen at a compression load of about 1500–2000 pounds for a time to fuse the stock completely to form a homogeneous melt which has lost memory of its former granular structure, then at about 150° C. placing the material under a compression load of about 12000–14000 pounds for another ten minutes to provide a melt in which the stock fuses completely and loses memory of its former granular structure, and cooling the resultant material to ambient temperatures under a compression load of about 1500 pounds to give a semicrystalline morphology which has no memory of the granular nature of original stock.

21. *A method for making an anisotropic meorphology of ultra-high-molecular-weight polyethylene comprising:* heating an original powder stock or a partially fused, melt-crystallized stock having granular memory, to a temperature between 220° C. and 320° C. in the absence of oxygen at a compress load of about 1500–2000 pounds for a time to fuse the stock completely to form a homogeneous melt which has lost memory of its former granular structure, then at about 150° C. placing the material under a compression load of about 12000–14000 pounds for another ten minutes to provide a melt in which the stock fuses completely and loses memory of its former granular structure cooling the resultant material to ambient temperatures under a compression load of about 1500 pounds to give a semicrystalline morphology which has no memory of the granular nature of the original stock, and extruding the semicryatalline product through an extrusion rolling die at a temperature of about 130° C. at a deformation ratio of about 5 to 8.

22. A method for making an anisotropic morphology of ultra-high-molecular-weight polyethylene comprising:

heating an original powder stock or a partially fused, melt-i crystallized stock having a granular memory, to a temperature between 220° C. and 320° C. in the absence of oxygen at a compression load of about 1500–2000 pounds for a time to fuse the stock completely to form a homogeneous melt which has lost memory of its former granular structure, then at about 150° C. placing the material under a compression load of about 12000–14000 pounds for another ten minutes to provide a melt in which the stock fuses completely and loses memory of its former granular structure, cooling the resultant material to ambient temperatures under a compression load of about 1500 pounds to give a semicrystalline morpholog which has no memory of the granular nature of the original stock, and drawing the semicrystalline product at a temperature of about 130° C. at a deformation ratio of about 5 to 8.

* * * * *